United States Patent [19]

Heckele

[11] Patent Number: 4,737,142
[45] Date of Patent: Apr. 12, 1988

[54] INSTRUMENT FOR EXAMINATION AND TREATMENT OF BODILY PASSAGES

[75] Inventor: Helmut Heckele, Knittlingen, Fed. Rep. of Germany

[73] Assignee: Richard Wolf GmbH, Fed. Rep. of Germany

[21] Appl. No.: 796,733

[22] Filed: Nov. 12, 1985

[30] Foreign Application Priority Data

Dec. 28, 1984 [DE] Fed. Rep. of Germany ....... 3443337

[51] Int. Cl.⁴ .......................... A61N 25/00; A61B 1/06
[52] U.S. Cl. ..................................... 604/95; 604/280; 604/282; 128/6
[58] Field of Search ........................ 604/95, 280–283, 604/96; 128/4–8; 350/96.2

[56] References Cited

U.S. PATENT DOCUMENTS

| 2,472,484 | 6/1949 | Krippendorf | 604/282 X |
| 4,207,874 | 6/1980 | Choy | 128/6 |
| 4,224,929 | 9/1980 | Furihata | 128/6 |
| 4,367,729 | 1/1983 | Ogiu | 128/6 |
| 4,448,188 | 5/1984 | Loeb | 604/962 |
| 4,465,481 | 8/1984 | Blake | 604/280 |
| 4,469,483 | 9/1984 | Becker et al. | 604/280 |

FOREIGN PATENT DOCUMENTS

| 930636 | 7/1973 | Canada | 604/281 |
| 2805451 | 8/1978 | Fed. Rep. of Germany . | |

*Primary Examiner*—Stephen C. Pellegrino
*Attorney, Agent, or Firm*—Hill, Van Santen, Steadman & Simpson

[57] ABSTRACT

An instrument for detection, examination and treatment of constrictions in bodily passages or vessels comprises a continuous-wall shaft in the form of a catheter having a small cross-section of up to 4 mm and having cross-sectionally distributed and longitudinally extending passages therethrough of identical or different cross-section, at least for the infeed and discharge of flushing liquids, bodily secretions or the like, for the passing through of auxiliary instruments and measuring elements and for reception of fibre light and fibre image guides.

10 Claims, 1 Drawing Sheet

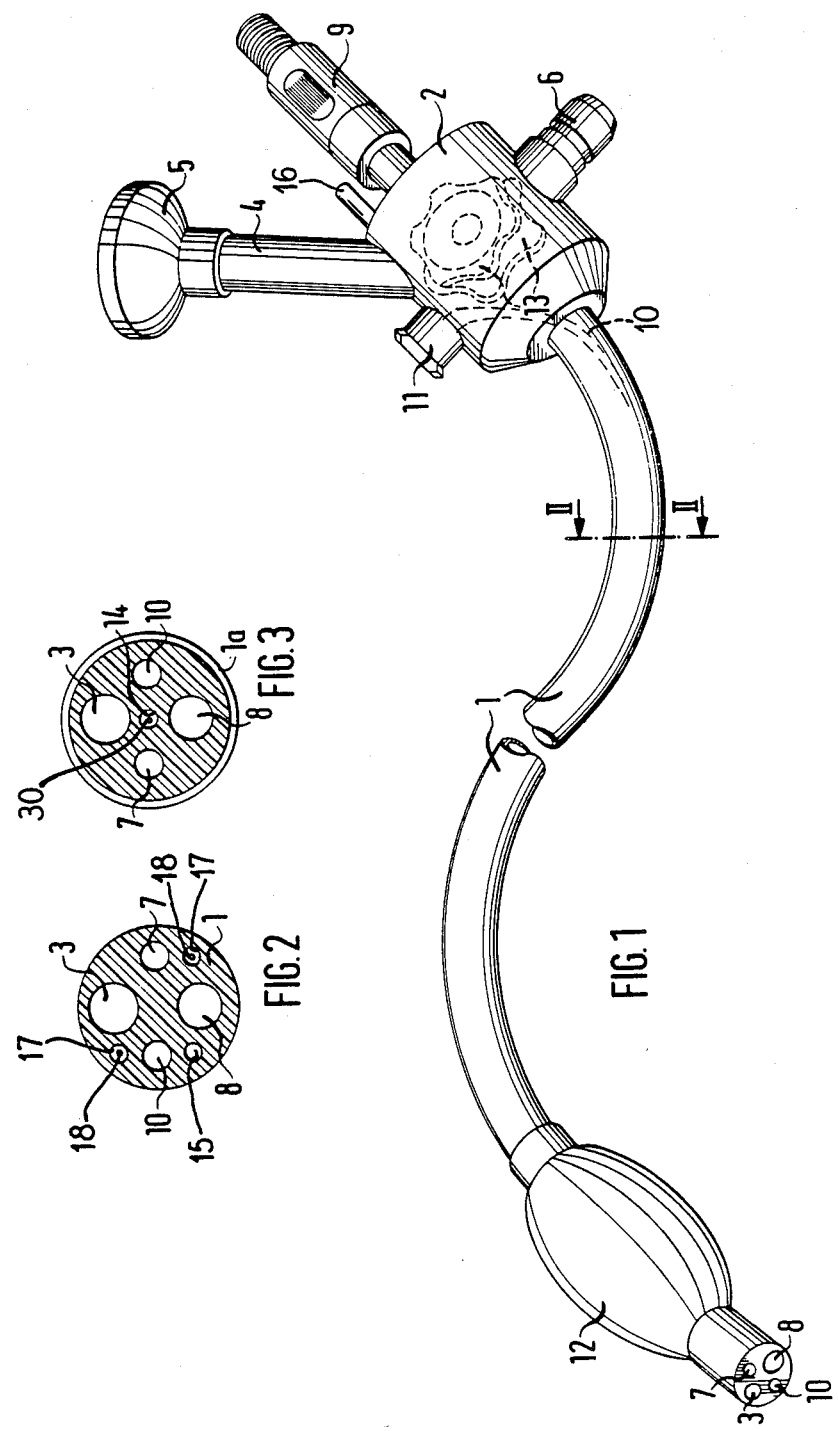

INSTRUMENT FOR EXAMINATION AND TREATMENT OF BODILY PASSAGES

BACKGROUND OF THE INVENTION

This invention relates to an instrument for examination and treatment of constrictions in bodily cavities or vessels.

DESCRIPTION OF THE PRIOR ART

It is known that constrictions in bodily passages or vessels may be eliminated by expansion by means of an inflatable balloon or the like, instead of treatment with medicines, or of installing a by-pass by means of an operation. The expansion by means of an inflatable balloon has hitherto had to be performed blind, so that the required precise position of the balloon in the constriction has not always been obtained. The fitting of a by-pass represents an operation unpleasent to a patient, with a protracted nursing home stay.

SUMMARY OF THE INVENTION

It is an object of the invention to provide a device for detecting stenoses or constrictions by direct visual examination in narrow bodily passages or vessels and in eliminating there, also under visual inspection.

This object is achieved in accordance with the invention by the provision of an instrument of the kind referred to in the foregoing comprising a flexible continuous-walled shaft, suitably of a type known in endoscopes, which is in the form of a catheter with a small diameter of up to 4 mm and has cross-sectionally distributed and longitudinally extending passages of identical or different cross-section, intended at least for the infeed and discharge of a flushing liquid, bodily secretions or the like, for the insertion of auxiliary instruments and measuring elements, and for reception of fibre light and fibre image guides.

By contrast to the hitherto required application of several single catheters for observation, treatment or flushing, it has been made possible for the first time according to the invention to provide a catheter having a small diameter which amounts to no more than about 4 mm, with several passages through which may be passed side-by-side fibre light and fibre image guides for observation, and instruments for elimination of these constrictions with inflow and outflow of flushing liquids, which naturally also have a very small diameter but no longer traverse separate shafts in the passages. The need for such additional shafts is prevented by the fact that the passage walls formed by the material of the continuous-wall shaft take over the guiding of all devices and auxiliary instruments which are to be inserted, instead of shafts.

It is known from German offenlegungsschrift No. 28 05 451, to construct the shaft of an endoscope as a continuous-wall or solid-wall shaft and to provide it with cross-sectionally distributed and longitudinally extending passages, in order to pass through fibre light and image guides as well as auxiliary instruments and to perform flushing actions by the inflow and outflow of flushing liquid. Endoscopes of this nature however normally have a greater diameter and are thus inappropriate to examine and eliminate constrictions in narrow bodily passages or vessels, since it has evidently not been considered possible by those skilled in this art to provide catheters having a small cross-section with diameters of up to 4 mm with several passages for observation and treatment purposes.

BRIEF DESCRIPTION OF THE DRAWINGS

The catheter according to the invention is described with other advantageous features and purposes of application with reference to the drawings. In these:

FIG. 1 shows a view in perspective of a catheter according to the invention, substantially enlarged, FIG. 2 shows an even more enlarged cross-section along line II—II of FIG. 1, FIG. 3 shows the same cross-section of a second embodiment with a shaft sheathing.

FIG. 4 is a perspective view of an embodiment of the catheter of the present invention;

FIG. 5 is a cross sectional view taken along line V—V of FIG. 4; and

FIG. 6 is a partial side view of the catheter illustrating the spatial or specific configuration.

DETAILED DESCRIPTION OF THE PREFERRED EMBODIMENTS

The catheter according to the invention comprises a solid-wall flexible shaft 1 of an appropriate well known clear plastic material having a memory which shaft has a small diameter of up to 4 mm and is inseparably immobilised in a proximal housing 2. The solid-wall shaft 1 is traversed by several passages, of which passage 3 for example is traversed by a fibre image guide having a distal window delimitation which passes through a proximal angle portion 4 of the housing 2 carrying an eyepiece 5. In FIG. 4, a second eyepiece 5' and a second portion 4' is provided and is arranged to be coaxially with the catheter. The housing 2 is also provided with a light junction connector 6 into which light is projected via a cable, which passes through a fibre light guide in another longitudinally extending shaft passage 7 and emerges at the distal end for illumination of the bodily passage or vessel. To this end, the fibre image light guides may be fixedly enclosed in the shaft 1 and may thereby form a part of the shaft. The solid-wall shaft may also consist of transparent plastics material and itself act as a light guide so that the passage 7 can then be omitted or freed for other purposes.

A third passage 8 serves the purpose of passing through auxiliary instruments or for passing through a laser fibre which is proximally connected to a longitudinally displaceable laser connector 9. Another passage 10 serves the purpose of feeding and discharging flushing liquids into and out of the bodily passage, via a connector stub 11. Just short of distal extremity, the flexible shaft 1 may be provided with a balloon 12, which is in contact with the shaft and inflatable, to allow the shaft to be immobilised within the bodily passage. To inflate the balloon 12, the balloon is connected by a passage 15 (FIG. 2) to an inflation or insufflation connection 16 on the control housing 2 (FIG. 1). Thanks to the flexible construction of the shaft 1, it is possible to allow other passages 17 to extend through the shaft, which receive traction wires or threads 18, which may be operated by handles 13 of the control housing 2 so that the distal extremity of the shaft 1 may be steered. In this connection, it may be advantageous to surround the shaft 1 as shown in FIG. 3 with an outer sheath 1a formed by one layer 20,21 (FIG. 5) or by several layers wholly overlapping each other in lengths diminishing by steps in the direction towards the distal shaft extremity, whereby the flexibility of the shaft and sheath diminishes from the distal towards the proximal extremity, so that the distal extremity is highly flexible, whereas the flexibility diminishes towards the proximal extremity and so that particularly advantageous steering or handling is rendered possible thereby.

The shaft 1 may be formed integrally of one material or divided into sections which establish an X-ray contrast and thereby also allow investigation by X-rays.

The shaft may be provided with a predetermined spatial form or curvature (see FIG. 6). By applying heat by a resistor wire 30 in a passage 14, the shaft will become elastic and lose the spatial form. With the dissipation of the heat from the shaft, it will be restored or returned to the specific spatial form.

What is claimed is:

1. An instrument for examination and treatment of constrictions in body passage and vessels, said instrument comprising a flexible continuous-wall shaft of solid clear plastic material in the form of a catheter with a diameter of not more than about 4 mm and having a plurality of cross-sectionally distributed and longitudinally extending passages in said material, at least one of said passages being for infeed and discharge of flushing liquids and bodily secretions, at least another of said passages being for the passing through of auxiliary instruments and measuring elements, and at least a third of said passages being for reception of a fibre image guide, the clear plastic material of said shaft forming means for conducting light along said shaft, and a elastically deformable sheath comprising a plurality of a partially overlapping layers surrounding the shaft, said shaft and the sheath having a flexibility which decreases from the distal end toward the proximal end of the catheter.

2. An instrument as claimed in claim 1, further comprising additional, longitudinal internal passages through said shaft containing control wires secured at the distal and proximal ends for omnilateral deflection of the distal end of the catheter, a control housing at the proximal end of said shaft and handles on said control housing for operation of said control wires.

3. An instrument as claimed in claim 1, further comprising a balloon adjacent the distal extremity of said shaft, a passage extending throughout the catheter length for inflation of said balloon and an insufflation connector situated on a control housing at the proximal end of the catheter and communicating with said inflation passage.

4. An instrument as claimed in claim 1, wherein the fibre image guide running through a shaft passage in said catheter is connected to an eyepiece set at an angle at the proximal end.

5. An instrument as claimed in claim 1, further comprising an eyepiece connected to the fibre image guide and arranged coaxially with the catheter at the proximal end.

6. An instrument as claimed in claim 1, wherein a laser attachment element receiving a laser fibre and displaceable in a longitudinally direction is situated at the proximal end of a control housing on the proximal end of the catheter shaft.

7. An instrument as claimed in claim 1, wherein said shaft has at least one section affording X-ray contrast for checking purposes.

8. An instrument for the examination and treatment of constrictions in body cavities and vessels, said instrument comprising a flexible catheter shaft of a solid transparent material having proximal and distal ends, said shaft having at least five passages extending between said ends and having an elastically deformable sheath means thereon, the sheath means creating a decreasing flexibility for said catheter shaft and sheath from the distal end to the proximal end; a control housing fixedly attached to the proximal end of said catheter shaft, said control housing having a light connector for connection to a light source, a connector stub for connection to a supply and drain for flushing fluids, an eyepiece projecting from a surface of the housing, an inflation connection for receiving an inflating medium and a control handle; said shaft being connected to the light connector on the control housing to form light guide means for conducting light to the distal end of the shaft; a fiber image guide extending through one of said passages in said shaft and being connected to said eyepiece projecting from said control housing; a second passage of said plurality of passages of the shaft forming a fluid passage extending longitudinally through said shaft and communicating with said connector stub of the control housing for supplying and receiving flushing fluids at the distal end of the shaft; a balloon on said shaft adjacent to the distal end, said balloon being connected to a third of the plurality of passages of said shaft, said third passage being connected to the inflation connection on the control housing, a fourth passage of the plurality of passages being an instrument passage extending longitudinally through the shaft and housing and at least one control wire extending longitudinally through a fifth passage of the shaft and being secured at its proximal end to the handle on the control housing and to the distal end of the shaft for steering the distal end of the shaft in response to movement of the handle on the control housing.

9. An instrument for examination and treatment of constrictions in a body passage and vessel, said instrument comprising a flexible continuous-wall shaft of solid clear plastic material having a memory, said material being convertible by an input of heat from a specific spatial form to an elastic state of a non-specific spatial form, said shaft being in the form of a catheter with a diameter of not more than about 4 mm and having a plurality of cross-sectionally distributed and longitudinally extending passages in said material, at least one of said passages being for the infeed and discharge of flushing fluids and bodily secretions, at least a second of said passages being for the passing through of auxiliary instruments and measuring instruments, at least a third of said passages being for reception of a fiber image guide, at least a fourth and fifth of the passages having control wires for steering the distal end of the shaft by operation of handles on a control housing attached to the proximal end of the shaft, a resistor wire extending in a sixth passage to each said shaft to cause the plastic material of the shaft to change to a nonspecific spatial form, said shaft forming means for conducting light along said shaft, and an elastically deformable sheath having a plurality of overlapping layers surrounding the shaft to decrease the flexibility of the shaft as one moves from the distal end towards the proximal end of the catheter.

10. An instrument for examination and treatment of constrictions in body passages and vessels, said instrument comprising a flexible continuous-wall shaft of solid clear plastic material in the form of a catheter with a diameter of not more than about 4 mm and having a plurality of cross-sectionally distributed and longitudinally extending passages in said material, at least one of said passages being for infeed and discharge of flushing liquids and bodily secretions, at least another of said passages being for the passing through of auxiliary instruments and measuring elements, and at least a third of said passages being for reception of a fibre image guide, the clear plastic material of said shaft forming means for conducting light along said shaft, said plastic material having a memory and being convertible by an input of heat from a specific spatial form to an elastic state of non-specific spatial form, and said shaft having a resistor wire received in one of the passages to heat said shaft.

* * * * *